(12) United States Patent
Albert et al.

(10) Patent No.: US 7,636,637 B2
(45) Date of Patent: Dec. 22, 2009

(54) VARIABLE LENGTH PROBE SELECTION

(75) Inventors: Thomas Albert, Madison, WI (US); Jason Norton, Madison, WI (US); Roland Green, Madison, WI (US)

(73) Assignee: Roche NimbleGen, Inc., Wilmington, DE (US)

( * ) Notice: Subject to any disclaimer, the term of this patent is extended or adjusted under 35 U.S.C. 154(b) by 577 days.

(21) Appl. No.: 11/156,439

(22) Filed: Jun. 20, 2005

(65) Prior Publication Data

US 2005/0282209 A1    Dec. 22, 2005

Related U.S. Application Data

(60) Provisional application No. 60/581,121, filed on Jun. 18, 2004.

(51) Int. Cl.
*G06F 19/00* (2006.01)
*C12N 15/11* (2006.01)

(52) U.S. Cl. ........................................ 702/20; 536/24.3

(58) Field of Classification Search ........................ None
See application file for complete search history.

(56) References Cited

U.S. PATENT DOCUMENTS

| | | | |
|---|---|---|---|
| 5,143,854 | A | 9/1992 | Pirrung et al. |
| 6,228,575 | B1 | 5/2001 | Gingeras et al. |
| 6,375,903 | B1 | 4/2002 | Cerrina et al. |
| 6,468,744 | B1 | 10/2002 | Cronin et al. |
| 2003/0235822 | A1 | 12/2003 | Lokhov et al. |

FOREIGN PATENT DOCUMENTS

WO    WO 01/05935 A2    1/2001

OTHER PUBLICATIONS

Albert et al. Light-directed 5'-3' synthesis of complex oligonucleotide microarrays. Nucleic Acids Research, vol. 31, p. e35 (2003).*
Anthony et al. Effect of Secondary Structure on single Nucleotide Polymorphism Detection wit a Porous Microarray Matrix; Implications for Probe Selection. BioTechniques vol. 34, pp. 1082-1089 (2003).*
Rouillard et al. (OligoArray 2.0: design of oligonucleotide probes for DNA microarrays using a thermodynamic approach. Nucleic Acids Research vol. 31, pp. 3057-3062 (2003).*
Hacia, J.G., "Resequencing and mutational analysis using oligonucleotide microarrays," Nature Genetics Supplement 21:42-47 (1999).
Saiki, R.K., et al., "Genetic analysis of amplified DNA with immobilized sequence-specific oligonucleotide probes," Proc. Natl. Acad. Sci. USA 86:6230-6234 (1989).
Anderson, M.L.M., "Hybridization Strategy," Gene Probe 2: A Practical Approach, Hames et al. (ed.), IRL Press, Oxford pp. 1-29 (1995).
Nuwaysir, E.F., et al., "Gene Expression Analysis Using Oligonucleotide Arrays Produced by Maskless Photolithography," Genome Research 12:1749-1755 (2002).
Wood, W.I., et al., "Base composition-independent hybridization in tetramethyl-ammonium chloride: A method for oligonucleotide...," Proc. Natl. Acad. Sci. USA 82:1585-1588 (1985).
Herold, Keith E. & Avraham Rasooly: Oligo Design: a computer program for development of probes for oligonucleotide microarrays; BioTechniques, vol. 35: 1216-1221 (Dec. 2003).
Singh-Gasson, Sangeet et al.: Maskless fabrication of light-directed oligonucleotide microarrays using a digital micromirror array; Nature Biotechnology, vol. 17: 974-978 (1999).

\* cited by examiner

*Primary Examiner*—John S Brusca
(74) *Attorney, Agent, or Firm*—Quarles & Brady LLP

(57) ABSTRACT

The present invention provides novel method for increasing the efficiency and accuracy of high-throughput mutation mapping and genome resequencing by using a variable length probe selection algorithm to rationally select probes used in designing oligonucleotide arrays synthesized by Maskless Array Synthesis (MAS) technology. Also disclosed is a variable length probe selection algorithm used in designing such oligonucleotide arrays.

7 Claims, No Drawings

VARIABLE LENGTH PROBE SELECTION

CROSS-REFERENCE TO RELATED APPLICATIONS

This application claims priority from U.S. provisional patent application Ser. No. 60/581,121 filed Jun. 18, 2004.

STATEMENT REGARDING FEDERALLY SPONSORED RESEARCH OR DEVELOPMENT

Not applicable.

BACKGROUND OF THE INVENTION

The advent of DNA microarray technology makes it possible to build an array of hundreds of thousands of DNA sequences in a very small area, such as the size of a microscopic slide. See, e.g., U.S. Pat. No. 6,375,903 and U.S. Pat. No. 5,143,854, each of which is hereby incorporated by reference in its entirety. The disclosure of U.S. Pat. No. 6,375,903, also incorporated by reference in its entirety, enables the construction of so-called maskless array synthesizer (MAS) instruments in which light is used to direct synthesis of the DNA sequences, the light direction being performed using a digital micromirror device (DMD). Using an MAS instrument, the selection of DNA sequences to be constructed in the microarray is under software control so that individually customized arrays can be built to order. In general, MAS based DNA microarray synthesis technology allows for the parallel synthesis of over 800,000 unique oligonucleotides in a very small area of on a standard microscope slide. The microarrays are generally synthesized by using light to direct which oligonucleotides are synthesized at specific locations on an array, these locations are called features. It is another advantage of the MAS microarray synthesis instrument that the designation of probes is under computer software control. This permits custom designed microarrays to be designed and executed with maximum flexibility as to the design of array probes, since difference probes can be made for each array, even for different arrays intended to assay the same genetic elements.

With the availability of the entire genomes of hundreds of organisms, for which a reference sequence has generally been deposited into a public data base, microarrays are being used to perform sequence analysis on DNA isolated from such organisms. One technique that can be used to identify a genetic variant is to sequence the genomic DNA of an individual and then to compare that sequence to the reference sequence of that organism. It has been found that many differences in DNA sequence are presented as single variations in DNA sequence, often referred to as single nucleotide polymorphisms or SNPs. The sequence comparison between the test genome and the reference genome of a species has been referred to as the brute force mechanism of capillary sequencing to identify the SNPs for a particular individual.

A key step and a more recent approach for identifying genetic variations associated with disease is the resequencing of candidate genes or other genomic regions of interest in patients and controls to identify those SNPs associated with a certain phenotype. (See Sakai et al., (1989) *PNAS* 86:6230-6234). A resequencing approach that has shown significant results utilizes oligonucleotide microarray technology (Hacia, et al., (1999) *Nature Genetics,* 21(1 Suppl):42-7.)

In particular, this type of array-based resequencing (ABR) approach depends on the differential hybridization of genomic fragments to short perfect-match (PM) and mismatch (MM) oligonucleotides. Each nucleotide to be queried is located at a central position of an oligonucleotide. For each PM oligonucleotide, probes representing the three possible mismatch nucleotides, one representing each possible SNP at the same central position are also synthesized on the array. The differences in hybridization signal intensities between sequences that bind strongly to the PM oligonucleotide and those that bind poorly to the corresponding MM oligonucleotides make is possible to discern the correct base at a given sequence position. Thus, in theory, any time a SNP is present, the mismatch probe representing this SNP will have a higher intensity signal than the corresponding probe that matches the reference sequence.

However, due to unpredictability in signal strength, varying hybridization efficiency, and various other sources of noise, this method typically results in many base positions whose identities are incorrectly predicted. For example, because all the array probes must be hybridized at the same temperature and hybridization stringency conditions, there can be problems with probes that have melting temperatures (Tm) that diverge significantly from the temperature at which the array is hybridized. For probes with a low Tm, the hybridized targets may be significantly washed off the array surface, producing little or no signal. For probes with a high Tm, the single base mismatch may not be significantly destabilizing to provide adequate discrimination to make robust base calls.

Another problem with single base discrimination is that the position of the mismatch can significantly alter the ability of a probe to provide significant discrimination to make robust base calls. For example, if the Tm of the portion of the probe on either side of the mismatch is very high, this portion of the probe may display robust hybridization independent of the mismatch, and thus not provide sufficient mismatch discrimination for base calling. As such, alternative approaches for increasing the efficiency and accuracy of array-based assays, such as DNA resequencing to identify mutations in the genomes of organisms would be a desirable contribution to the art.

BRIEF SUMMARY OF THE INVENTION

The present invention is summarized as a novel method for increasing the efficiency and accuracy of high-throughput mutation mapping and genome resequencing by using a variable length probe selection algorithm to rationally select probes used in designing oligonucleotide arrays. The present invention thus provides a method and an algorithm for rationally varying oligonucleotide probe length to enable accurate single base mismatch discrimination in large scale resequencing projects.

In one aspect, the invention provides a method for producing a microarray having a series of features comprising a plurality of variable length oligonucleotide probes, the method including the steps of: selecting a plurality of variable length oligonucleotide array probes, wherein the variable length probes are derived by inputting a minimum probe length, a maximum probe length, and a target melting temperature for a plurality of oligonucletide array probes into a probe selection algorithm; wherein the algorithm is capable of calculating variable oligonucleotide probe lengths, wherein all of the probes exhibit the following characteristics: (i) similar melting temperature and (ii) mismatch position in each probe that is located at the approximate thermodynamic center of each probe; synthesizing an array of oligonucleotide probes having varying lengths on a feature of the microarray using Maskless Array Synthesis (MAS); and producing the microarray having a series of features having a plurality of variable length oligonucleotide probes.

An aspect of this method is that it provides increased mismatch discrimination for base calling as compared to probes which do not have the above characteristics.

In another aspect, the invention provides that the target Tm is achieved by increasing the length of the probes having a low Tm and decreasing the length of the probes having a high Tm.

In another aspect the invention provides that the variable length oligonucleotide array probes have similar melting temperatures and a mismatch position in each probe that is held at the approximate thermodynamic center of each oligonucleotide.

In this aspect of the invention oligonucleotide probes with a low Tm are made longer and probes with a high Tm are made shorter.

In another aspect the invention provides for a probe selection algorithm, which is capable of accepting minimum and maximum probe length data along with target Tm for all the probes on the array.

In this aspect of the invention, the target Tm of a probe of interest is divided in half and each portion of the probe on either side of the mismatch can be varied in length, so as to stay within the specified length parameters and to reach half of the specified target Tm.

In this aspect of the invention the probe Tm is calculated using the formula: Tm=5*(Gn+Cn)+1*(An+Tn), where the n is the number of each specific base present in the probe.

Other objects advantages and features of the present invention will become apparent from the following specification.

BRIEF DESCRIPTION OF THE SEVERAL VIEWS OF THE DRAWINGS

Not applicable.

DETAILED DESCRIPTION OF THE INVENTION

The present invention broadly provides a novel method for increasing the efficiency and accuracy of high-throughput mutation mapping and genome resequencing by using a variable length probe selection algorithm to rationally select probes used in designing oligonucleotide arrays. Specifically, the invention provides a solution to the problem of insufficient mismatch discrimination for base calling in large scale array-based resequencing by rationally varying the length of the oligonucleotide probes. To do this we developed a variable length probe selection algorithm that performs the functions of enabling the probes with a low Tm to be made longer, and probes with a high Tm to be made shorter, and at the same time maintaining the mismatch position in each probe at the thermodynamic center of the oligonucleotide. This approach differs from prior approaches which typically vary on the sequence of the probes, with all probes being the same length.

In accordance with the invention, one embodiment provides a method for producing a microarray having a series of features comprising a plurality of variable length oligonucleotide probes, the method comprising the steps of: selecting a plurality of variable length oligonucleotide array probes, wherein the variable length probes are derived by inputting a minimum probe length, a maximum probe length, and a target melting temperature for a plurality of oligonucletide array probes into a probe selection algorithm. The algorithm is capable of calculating variable oligonucleotide probe lengths, wherein all of the probes exhibit the following characteristics: (i) similar melting temperature and (ii) mismatch position in each probe that is located at the approximate thermodynamic center of each probe; synthesizing an array of oligonucleotide probes having varying lengths. Such an array is best manufactured using a Maskless Array Synthesis (MAS) instrument which enables producing a microarray with a series of features having variable length oligonucleotide probes.

To use common terminology throughout, we will use probe to mean the normally single stranded nucleic acids molecules synthesized as a part of the microarray and typically tethered at one to a substrate. The probes are of defined sequences and all of the probes in a defined area are of a common sequence, that area of probes of the same common sequence being called a feature of the microarray. Obviously, in accordance with the present invention the probes will be of different length, but usually all of the probes in a single feature will be of the same length. Using the MAS instrument, it is practical to construct microarrays with probes as long as 75 to 100 nucleotides in length with usable fidelity.

In another embodiment, the invention provides a method for solving insufficient mismatch discrimination for base calling by rationally varying the length of the oligonucleotide probes using a variable length probe selection algorithm which selects probes having a similar Tm and at the same time a probe mismatch position that is at the thermodynamic center of the oligonucleotide. To perform these two functions simultaneously, the method of the invention uses an algorithm which is capable of accepting input data from the user to specify the minimum and maximum probe lengths, and the target Tm for all the probes on the array. The target Tm of the probe is then divided in half, and each portion of the probe on either side of the mismatch is varied in length, to both stay within the specified length parameters, and to reach half of the specified target Tm. The following equation was used to calculate the probe Tm:

Probe $Tm=5*(G_n+C_n)+1*(A_n+T_n)$, wherein the n is the number of each specific oligonucleotide base (G, C, A or T) present in the probe. However, it is envisioned that any equation for determining probe temperature could be used in conjunction with the novel strategy for varying the probe length to improve mismatch discrimination for base calling.

Accordingly, another embodiment of the invention is a variable length probe selection algorithm for the design of oligonucleotide arrays for genome resequencing projects. Use of the variable length probe selection algorithm is to produce array probes that all have a similar Tm and a mismatch position which is held at the approximate thermodynamic center of each oligonucleotide, where it is theoretically the most destabilizing.

The following examples are provided as further non-limiting illustrations of particular embodiments of the invention.

EXAMPLES

Sequencing and Resequencing of 10,000 Bases of the SARS Coronavirus Genome

In order to resequence ~10,000 bases of the SARS coronavirus genome, the genomic DNA from SARS was amplified, digested and labeled as described below. For example, 1 µg of S SARS was amplified in several reactions using multiplex PCR, resulting in 1 µg of amplified DNA. For each array hybridization, 100 ng of amplified genomic DNA was digested with 0.1 U DNase I (Amersham Biosciences, Piscataway, N.J.) and 1× One-Phor-All buffer (Amersham) in a total volume of 20 µL. DNase I was inactivated by incubation at 97° C. for 15 minutes. Sample was end-labeled with 1 µL Biotin-N6 ddATP (Perkin Elmer, Wellesley, Mass.) and 25 U Terminal Deoxynucleotidyl Transferase (Promega, Madison, Wisc.) at 37° C. for 90 minutes, and terminal transferase was inactivated by incubation at 97° C. for 15 minutes.

Before application of the labeled sample to the array, the resequencing arrays were pre-hybridized with 1× NimbleGen Resequencing Buffer (NimbleGen Systems, Madison, Wisc.). Samples were heated to 95° C. for 5 minutes, heated to 45° C. and centrifuged for 5 minutes at >12000 g. Each labeled DNA sample was then applied to the arrays, which were placed in a customized hybridization chamber and incubated at 45° C. for 14 to 16 hours in a rotisserie oven. The arrays were then washed with nonstringent wash buffer (6× SSPE, 0.01% [v/v] Tween-20), followed by two 5 minute washes in stringent wash buffer (100 mM MES, 0.1 M NaCl, 0.01% [v/v] Tween-20) at 47° C. The arrays were stained with a solution containing Cy3-Streptavidin conjugate (Amersham Biosciences, Piscataway, N.J.) for 10 minutes, and washed again with nonstringent wash buffer. The Cy3 signal was amplified by secondary labeling of the DNA with biotinylated goat anti-streptavidin (Vector Laboratories, Burlingame, Calif.). The secondary antibody was washed off with non-stringent wash buffer, and the array was re-stained with the Cy3-Streptavidin solution. Finally, the stain solution was removed, and array was washed in non-stringent wash buffer followed by a 30 seconds wash in 0.5×SSC and 15 seconds wash in 70% ethanol. Arrays were spun dry in a custom centrifuge and stored prior to being scanned.

Microarrays were then scanned at 5 μm resolution using the Genepix® 4000b scanner (Axon Instruments, Inc., Union City, Calif.). The image was interpolated and scaled up 2.5× in size using NIH Image software (http://rsb.info.nih.gov/nih-image/), and pixel intensities were extracted using NimbleScan™ Software (NimbleGen Systems, Inc. Madison, Wisc.). Sequence calls were made based on statistical analysis of the hybridization intensities combining data from both strands using a preferred, novel Machine-Learning algorithm that utilizes a classification technique called K-nearest-neighbors. The arrays were then scanned and images were extracted as described above.

Comparison of the Single vs. Variable Probe Lengths

The variable length probe selection algorithm was tested by comparing both the single probe lengths with the variable length probe selection algorithm at varying target probe Tms by designing probes to resequence ~10,000 bases of the SARS coronavirus genome.

Genomic DNA from the SARS were amplified, digested, labeled and resequenced as described above. The sample was then hybridized to an array. It is noted that the number of array sets in any particular experiment can vary depending on the size of the genome being analyzed.

To determine the best probe selection technique, the number of non-conforming bases was calculated for each probe selection criterion. As referred to herein a "conforming base" is a base that is called or assigned by the array to be identical to that of the base in the reference virus sequence. Also, as used herein a "non-conforming base" is a base that is called or assigned to be different from the corresponding base in the reference sequence. Therefore, if the system is behaving perfectly, all bases will conform to the reference. The probe selection algorithm that produces the fewest number of non-conforming bases produces the best experimental results. The following table lists the actual resequencing results using several probe selection criteria:

TABLE 1

| Probe Length | Non-Conforming Base Calls |
|---|---|
| 29 mers | 203 |
| 33 mers | 45 |
| 37 mers | 37 |
| 29–39 mers Tm92 | 14 |
| 29–39 mers Tm86 | 12 |
| 29–39 mers Tm78 | 8 |
| 29–39 mers Tm72 | 7 |

Table 1 clearly shows that the variable length probe selection algorithm is superior to the uniform length probes. Furthermore, by setting the target Tm to 72° C., the lowest number of non-conforming base calls was observed, resulting in the best or most accurate mismatch discrimination for base calling of the tested criteria.

Furthermore, applicants envision that the variable length probe selection algorithm for designing oligonucleotide arrays can be utilized in any resequencing project, such as comparative genomic resequencing, used for identifying mutations in haploid species or a haploid preparation of a diploid genome. The invention may also be helpful for large resequencing projects that use BACs (bacterial artificial chromosomes, having an average size of 1000 kb), plasmids, phosmids, YACs (yeast artificial chromosomes) or any other library or preparation that results in the isolation of haploid sections of a genome.

It is understood that certain adaptations of the invention described in this disclosure are a matter of routine optimization for those skilled in the art, and can be implemented without departing from the spirit of the invention, or the scope of the appended claims.

We claim:

1. A method for producing a microarray for identifying nucleotide polymorphisms in a sample, the microarray having a plurality of features comprising copies of an oligonucleotide probe having an overall probe length no shorter than a minimum length and no longer than a maximum length and having a nucleotide mismatch relative to a reference sequence, the method comprising the steps of:

for each probe, determining a probe length upstream of the mismatch and a probe length downstream of the mismatch, such that the overall probe length differs between features but the probe at each feature has a melting temperature (Tm) when bound to a nucleic acid molecule in the sample that is approximately equal to a target Tm, wherein the upstream- and the downstream probe lengths of each probe contribute about equally to the Tm of the probe;

synthesizing the features on a substrate to produce the microarray.

2. The method of claim 1 wherein the target Tm is achieved in the determining step by increasing the length of probes having a low Tm and decreasing the length of probes having a high Tm relative to a mean Tm of the probes.

3. The method of claim 1 wherein the probe Tm is calculated using the formula: $Tm=5*(G_n+C_n)+1*(A_n+T_n)$, where the n is the number of each specific base present on the probe.

4. The method of claim 1 wherein the microarray is used in array-based genome resequencing.

5. The method of claim 1 wherein the synthesizing step is performed by maskless array synthesis.

6. A microarray comprising:
a substrate;
a plurality of features comprising copies of a single-stranded nucleotide probe tethered at one end to the substrate, the probe having a nucleotide mismatch relative to a reference sequence and a melting temperature (Tm) approximately equal to a target Tm when bound to a nucleic acid molecule having the nucleotide mismatch, a probe length upstream of the mismatch and a probe length downstream of the mismatch contributing about equally to the probe Tm;
the probes differing in length between features.

7. A method for producing a microarray having a series of features comprising a plurality of variable length oligonucleotide probes, the method comprising the steps of:
selecting a plurality of variable length oligonucleotide array probes, wherein the variable length probes are derived by inputting a minimum probe length, a maximum probe length, and a target melting temperature for a plurality of oligonucleotide array probes into a probe selection algorithm; wherein the algorithm is capable of calculating variable oligonucleotide probe lengths, wherein all of the probes exhibit the following characteristics: (i) similar melting temperature and (ii) mismatch position in each probe that is located at the approximate thermodynamic center of each probe; and
synthesizing a microarray of oligonucleotide probes with the length of the probes determined by the selecting step so that the length of probes in some features is different than the length of probes in other features,
wherein the target Tm for each of the plurality of array probes is divided in half, and each half of the probe on either side of the mismatch position is independently varied in length, so as to stay within the minimum and maximum probe length parameters and to achieve half of the target Tm.

* * * * *

UNITED STATES PATENT AND TRADEMARK OFFICE
CERTIFICATE OF CORRECTION

PATENT NO.       : 7,636,637 B2                                          Page 1 of 1
APPLICATION NO.  : 11/156439
DATED            : December 22, 2009
INVENTOR(S)      : Albert et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1002 days.

Signed and Sealed this

Ninth Day of November, 2010

David J. Kappos
*Director of the United States Patent and Trademark Office*